United States Patent

Antonson et al.

[11] Patent Number: 6,066,274
[45] Date of Patent: May 23, 2000

[54] METHOD AND MEANS FOR PRODUCING A CERAMIC OR METALLIC PRODUCT FOR SINTERING

[75] Inventors: Izidor Antonson, Partille; Jesper Brandt, Göteborg; Robert Pompe, Molndal, all of Sweden

[73] Assignee: Nobel Biocare AB, Sweden

[21] Appl. No.: 08/981,706

[22] PCT Filed: Jun. 24, 1996

[86] PCT No.: PCT/SE96/00819

§ 371 Date: Mar. 23, 1998

§ 102(e) Date: Mar. 23, 1998

[87] PCT Pub. No.: WO97/01408

PCT Pub. Date: Jan. 16, 1997

[30] Foreign Application Priority Data

Jun. 28, 1995 [SE] Sweden .................................. 9502338

[51] Int. Cl.[7] .............................. A61C 13/00; B22F 3/00
[52] U.S. Cl. ........................... 264/16; 264/219; 264/225; 425/78; 425/175; 425/547
[58] Field of Search ............................ 264/16, 219, 225; 419/38, 65, 66; 425/78, 175, 547; 249/54

[56] References Cited

U.S. PATENT DOCUMENTS

| | | | |
|---|---|---|---|
| 4,039,697 | 8/1977 | Isawa et al. | 427/27 |
| 5,405,570 | 4/1995 | Fuma et al. | 419/2 |
| 5,435,967 | 7/1995 | Nishikawa et al. | 419/65 |
| 5,498,382 | 3/1996 | Seitz et al. | 264/56 |
| 5,624,604 | 4/1997 | Yasrebi et al. | 252/313.1 |
| 5,665,289 | 9/1997 | Chung et al. | 264/628 |

FOREIGN PATENT DOCUMENTS

| | | |
|---|---|---|
| 0 115 104 | of 1984 | European Pat. Off. . |
| 0 231 773 A1 | of 1987 | European Pat. Off. . |
| 0 664 998 A1 | of 1995 | European Pat. Off. . |
| 0 688 746 A1 | of 1995 | European Pat. Off. . |
| 514412 | of 1971 | Switzerland . |
| 1276731 | of 1972 | United Kingdom . |

*Primary Examiner*—Christopher A. Fiorilla
*Attorney, Agent, or Firm*—Pollock, Vande Sande & Amernick, R.L.L.P.

[57] ABSTRACT

A device including an injection molding tool for use once or a few times for producing a sinterable ceramic and/or metallic product. The device includes at least one first tool part. At least one second tool part is combinable with the at least one first tool part to form a molding space for the product. The second tool part is produced using a wet composition and is made of a readily worked and form-stable material containing pores and admixed heat-conducting particles. A wet composition-enclosing member can engage the first tool part during the production of the second tool part. A unit can be connected to the at least one second tool part and can be arranged with the at least one first tool part for absorbing internal lateral displacement forces arising during squeezing or injection of an injection molding composition. The injection molding tool is adapted to receive an injection molding composition containing a ceramic and/or metallic powder that is introduced into the molding tool with low or medium pressure for forming the product. The pores and the admixed heat-conducting particles conduct away heat generated during the molding and gas trapped in the molding space. The pores also provide a well-balanced porosity for effecting conduction of the gas and, together with a flexibility in the solidified injection molding composition, permit the product to be separated from the tool parts without braking.

20 Claims, 1 Drawing Sheet

METHOD AND MEANS FOR PRODUCING A CERAMIC OR METALLIC PRODUCT FOR SINTERING

This application is a U.S. National Application of PCT/SE96/00819, filed Jun. 24, 1996.

TECHNICAL FIELD

The present invention relates, to among other things, a process for producing a sinterable ceramic or metallic body, which can also have an individual and distinctive shape and, for example, consists of a dental bridge shell. The production is executed using a tool/molding tool which can be assembled from two or more tool parts and whose molding space corresponds to the shape of the body. The invention also relates to a device or tool for producing the sinterable ceramic or metallic product or ceramic prosthesis (metallic prosthesis). Furthermore, the invention relates to a process for producing a shell for a metallic or ceramic product or a ceramic prosthesis (metallic prosthesis) which is designed to be anchorable to a base which has been prepared in the human body and, for example, includes or consists of an implant, tooth remnant(s), etc. In the process, use is made of a tool having a molding space for the shell and of first and second models of the base and the shell, respectively. The invention also relates to an injection molding tool for the product or prosthesis. The invention also relates to a process for producing an injection molding composition, which comprises a polymer melt and/or wax, melt (binding agent) and powder particles mixed into this melt. The composition is intended to be squeezed or pressed, in the melted state, into one or more spaces in an injection molding tool to achieve a sinterable body which is formed when the composition is in solidified form and which preferably has an individual and/or complex shape. In addition, the invention relates to a powder for an injection molding composition which, in the melted state, can be squeezed or injected under low or medium pressure, by which in this case is meant 1–200 bar, into one or more molding spaces in an injection molding tool for the purpose of forming a sinterable solidified body which preferably has an individual and/or complex shape. Finally, the invention relates to an injection molding composition for forming, in a tool, a sinterable body which preferably has an individual and/or complex shape. The composition comprises a sinterable powder which has been treated with a hydrophobic agent and can be mixed into a melt of binding agent, for example paraffin wax and/or polyethylene. The invention can also be used for making products in metal/hard metal, with use being made of metal powder, for example titanium powder, which is molded and sintered to the desired density.

BACKGROUND OF THE INVENTION

The production of ceramic products or ceramic prostheses is very well known. Thus, for example, it is known to make use of die casting employing a tool which has a porous tool part through whose pores solvent, which has been released, is conducted away during the casting process. When producing dental bridges, for example, it is already known to use models of jawbone impressions and dental bridge shapes for producing dental bridge shells, which are to be coated with additional material for aesthetic shaping. It is also known to produce tools and tool parts to which the shape of the product or prosthesis can be transferred using a copying technique, after which the tool or tool part is used for spark machining a workpiece to form the product or prosthesis.

It is also well known to produce different types of wet compositions containing solvents and plaster and to use these in connection with making ceramic products in the form of coffee pots, lavatory seats, exhaust ports for internal combustion engines, etc. In this context, it is known to propose injection molding compositions which include ceramic powder or metallic or alloy powder which can be mixed into the melt of binding agent in the form of wax, polymers, etc. In connection with this, well-known technology proposes the use of dry crushing processes, dispersing agents, etc.

The body/product/prosthesis which is referred to above and which is produced using the present invention must be sinterable. The sintering confers the desired hardness on the body during the course of a certain degree of shrinkage. Such sintering is well known and is not part of the subject-matter of the present invention.

In connection with production of the product, there is a need for a technically simple tool for producing one or a few products, for example when making dental products, manufacturing prototypes, making products in small series, etc. In this context, the tool must have a technical construction, which permits economic use. The sole product, or the few products, must themselves carry the tool costs, which, in the case of dental bridge production, for example, implies a tool cost of only 20–30 SEK/product, calculated at present-day prices. The use of present-day technology and the manufacture of tool parts in, for example, high speed steel and the like results in a cost which is many times greater and which makes it impossible to produce the tools as disposable tools. This is one of the problems the invention is intended to solve.

In, for example, the production of dental products having individual and often complicated shapes, for example dental bridge shells, there is need to obtain a sinterable body/dental bridge, while retaining the high demands for fit which are placed on this body/dental bridge, by means of a single treatment step (molding). For example, it is difficult, when casting ceramic bodies, to prevent these bodies from buckling, which results in poor fitting shape. In accordance with the present invention, these problems are solved by special tool construction, tool production and a specially indicated injection molding composition.

Especially in the production of dental bridges, there is a general requirement for simplified methods for producing individually shaped products/bodies with a high degree of precision. The invention also provides solutions to this problem and makes it possible to create, in one and the same tool assembly, the underside and external contours of a body/dental bridge, which can extend between two or more teeth/attachment points in the dentine. In doing this, it is possible to avoid previous problems involved in creating bodies in several manufacturing steps, in which the external shape is transferred via a copying function is and the internal shape is produced by means of spark machining using a tool(s) to which the internal shape has previously been transferred by means of copying.

In connection with the injection molding of a product having a complicated shape, there is a need for heat to be conducted away in an efficient manner and for preventing distortion of the result by air cushion(s) which is/are trapped in the molding space. These problems, too, are solved by the invention, which proposes a specific heat-removal function using a heat conducting metal or alloy particles of specific quantity which are mixed into a tool part and which ensure that heat is conducted away in an appropriate manner. Thus, a well-balanced porosity in the tool part guarantees that air is removed in an appropriate manner from the molding space during the molding of the product. A porosity, which is too low, does not provide sufficient removal of air, and a porosity which is too high, with pore channels which are too large, results in the injection molding composition flowing out into the tool part.

When producing a tool part as described above, a wet composition is used whose solvent (water) is driven off by drying under ambient conditions or at an elevated temperature.

The demand placed on the material in the tool part, which is produced using the wet composition, is that it exhibits the properties, which are required as regards the injection molding and other aspects of the production. Thus, for example, the composition must be easy to shape or pour and, in the solidified state, exhibit shape-stability properties within given areas. It must be possible for the chemical reaction to take place at room temperature and it must be possible to regulate the porosity by means of pressure and temperature. The invention also solves these problems and recommends, as an example, that the modulus of elasticity should be>1 GPa in the solidified material.

There is a need, in this connection, to obtain a coherent, sinterable body as the result of the injection molding. In addition, it must be easy to separate the body from the tool part, i.e. the material in the body must exhibit a certain flexibility so that the injection-molded body does not break when being separated from the tool part or tool parts. This places demands on the make-up of the injection molding composition, which, in addition, must be such that confluence or chemical reaction with the tool part produced from the wet composition does not take place. The invention also solves this problem.

In the production of the injection molding composition and the powder for this composition, it is essential that the powder agglomerate can be broken up and that preparation of the powder takes place in such a way that optimal homogeneity of the composition, without contamination, can be achieved using a limited number of process steps. It must be possible to hydrophobicize the powder surfaces efficiently by removing the excess of absorbed water. The dry matter content of the powder before it is mixed into the polymer melt and/or wax melt must be high, and it is advantageous if the energy consumption can be held down during the course of the admixing. The invention also solves these problems and proposes an effective preparation process prior to the admixture with the wax and/or the polymer.

SUMMARY OF THE INVENTION

The present invention is characterized in that at least one tool part is produced from a wet composition which comprises solvent, heat conducting particles and material which is easy to work and whose shape is stable in solidified form. The material is caused to solidify in a binding function (for example chemical reaction), after which the solvent is driven off by drying and a pore channel system is thereby formed in the solidified material. During the solidification, a part of the shape of the body is transferred to the tool part or the solidified material. The remaining shape or shapes of the body is/are transferred to the other tool part(s). Sinterable injection molding composition is injected or squeezed into the molding space using a low or medium compression molding pressure, by which, in this case, is meant a compression molding pressure of between 1–200 bar. Heat which arises due to the injection molding composition which has been injected into the molding space is conducted away by means of the heat-conducting particles in the solidified material. Gas or air which is trapped in the molding space during the injection or the squeezing-in is conducted away through the pores in the solidified material.

An injection molding tool for carrying out the process is arranged with at least one tool part made of material which is readily worked and form-stable, examples of such material which may be mentioned in this context being plaster, cement, aluminum phosphate-bound or sol-bound (so-called cold bound) ceramic mixtures, sintered porous metal/ceramic mixtures, etc. The material must contain pores and admixed heat-conducting particles which are to form a heat-removal network for the heat. The tool part can be combined with one or more other tool parts in order to form one or more molding spaces for the product(s)/prosthesis (prostheses). The injection molding tool is arranged, in connection with the formation of the sinterable product or prosthesis, to receive an injection molding composition which is squeezed in using a low pressure or a medium pressure and which contains a sinterable ceramic powder or metallic powder. Heat, which is generated during the molding, and gas or air, which is trapped in the molding space, can be conducted away with the aid of the heat-conducting particles and the pores, respectively.

The process for producing a shell for a ceramic product (metallic product) or ceramic prosthesis (metallic prosthesis) which uses a tool having a molding space for the shell and first and second models of a base which is allocated to the shell and the shell, respectively, is principally characterized in that the first model is applied to a tool part and a first delimitation surface is thereby formed with the upper shape or upper surface of the base. The second model can be applied to the first model from the outset or can be applied to the first model at the time of or during the production. A member, which forms a molding space, is applied or arranged around at least the first model in the tool parts. A wet composition containing heat-removing particles is applied to the molding space of the member so that second model is enclosed by the wet composition. The latter is caused to solidify and the solidified material is allocated the function of a second tool part which can cooperate with the first tool part, in which second tool part the second delimitation surface of the molding space is formed by the outer shape or upper surface of the second model. After that, the first and second tool parts are separated and the second model is removed. The tool parts are brought together once again and means for forming the shell are injected or squeezed into the molding space which is thereby formed, with heat removal being effected by way of the heat-removing particles.

An injection-molding tool for the process is characterized in that the first tool part is arranged to support a first model of the base (the jaw) which is to support the shell or equivalent dental product. In this context, the base forms, by means of its upper parts, a first delimitation surface for the molding space. A second model, which corresponds to the shape of the shell or the dental product, can be applied to the first model. The second tool part is formed out of or with solidified wet composition which is applied at least around and to enclose the second model when the latter assumes its position on the first model. The second model can then be removed from the first model in order to form the molding space. The shell can be produced by means of injection molding composition which is injected or squeezed into the molding space which has thus been established. Heat removal during the injection or squeezing-in is arranged to take place by way of the heat-conducting particles which are admixed with the solidified wet composition.

The process which was mentioned at the outset for producing an injection molding composition is principally characterized in that, before the powder particles are mixed into the melt, the water which is absorbed by the surfaces is driven off so that a high degree of drying is achieved. In this context, a high degree of drying is to be understood as meaning that at most 5–20 percent of the original quantity of water remains. After that, the powder particle surfaces are coated with one or more agents, for example stearic acid, by means of which agent or agents the particle surfaces are hydrophobicized while, at the same time, deagglomerating and lubricating functions are implemented in the injection molding composition both for the mutual separation (and better admixture) of the powder particles and for facilitating the introduction of the composition into the respective molding space using squeezing-in or injection members. After that, the powder having a high dry matter content can be mixed into the melt.

A powder for the injection molding composition has the powder particles dried in order to obtain particle surfaces which are free from physically adsorbed water, in particular, and the particle surfaces are coated with one or more agents, for example stearic acid. The agent has a hydrophobicizing effect and brings about deagglomeration and lubricating functions which keep the particles apart and, respectively, facilitate injection and/or squeezing into each space of the spaces. The powder can be mixed with polymer and/or wax (for example paraffin wax) which contains binding-agent melt.

Hydrophobicization of the particle surfaces is preferably brought about mechanically by, for example, mixing the powder and hydrophobicizing additives in a vessel in the presence of milling media on a drum bench. The size, quantity, hardness and form of the milling media can be chosen so that the milling effect is avoided. The task of the milling media is to effect abrasion of the particle surfaces, thereby creating reactive surfaces for binding between the particles and the hydrophobicizing medium which has been supplied. This binding is important for keeping the particles apart during the mixing process. In other cases, milling media having a high degree of hardness and increased size and quantity are chosen in order, apart from bringing about the abovementioned effect, also to bring about a simultaneous milling effect, i.e. decrease in the size of particles.

An injection molding composition according to the invention is also characterized in that the proportion of wax in the solidified body substantially exceeds the proportion of polyethylene, and in that the latter proportion is only 1–10 percent volume of the former proportion.

By means of that which has been proposed above, technically efficient manufacture of dental products (dental bridge shells) and prototypes can be achieved employing tools which are used only once or just a few times. The cost of producing the tools is minimal and very attractive from the industrial point of view. The processes involved in producing the product can also be considerably simplified and do not require any additional measures arising from the use of the new type of tool. The injection molding composition can be arranged to be technically easy to prepare, using elements of is conventional production processes in which the preparation is characterized by technical simplicity and good economy. The production of wet compositions for one or more tool parts (even all of them) is effected using techniques and material with which the dental technician or equivalent is thoroughly familiar. The removal of injection-molded, sinterable products from each tool part is simplified and ensured in a reliable and effective manner.

BRIEF DESCRIPTION OF THE DRAWINGS

A presently proposed embodiment of the process, devices and joint fillers/powders will be described below while at the same time referring to the attached drawings in which.

DETAILED DESCRIPTION OF THE PREFERRED EMBODIMENT(S)

Figure 1:
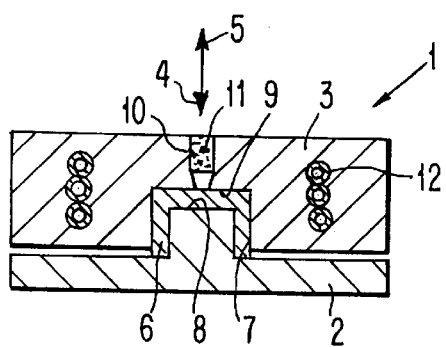
FIG. 1 shows, in vertical section, an example of the construction of a tool.
Figure 2:
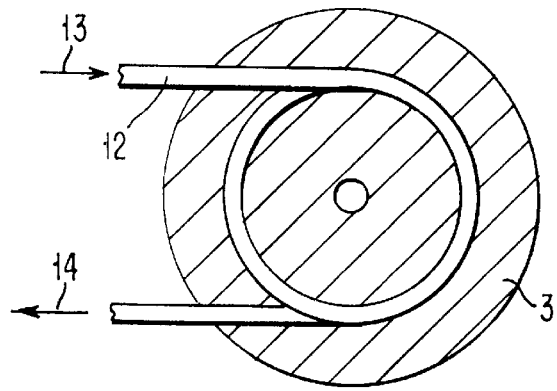
FIG. 2 shows the tool according to FIG. 1 in horizontal section.
Figure 3:
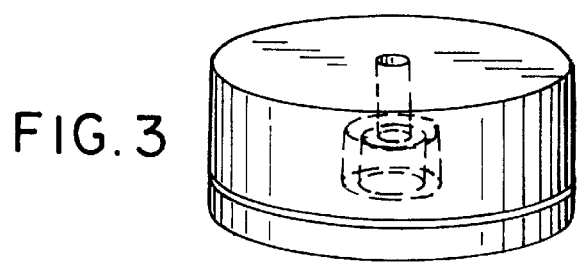
FIG. 3 shows the tool according to FIGS. 1 and 2 in perspective obliquely from above.

An injection-molding tool, designated by 1, is shown diagrammatically in FIG. 1. The tool comprises a lower tool part 2 and an upper tool part 3. The tool parts can be brought towards and away from each other, in the directions of arrows 4, 5. The tool represents the injection molding of a body 6 having a simple shape, for example a cylindrical body (body shape) which is provided with a bottom part. The body (body shape) is produced in the mold 7 of the tool which is formed by the tool surfaces 8, 9. A channel for injection molding composition is shown by 10. The tool part 3, and, where appropriate, the part 2 as well, contain, in their material, baked-in heat-conduction particles which can consist of aluminum particles, alloy particles, bronze particles, etc. The particles form a network in the material for the purpose of effecting heat removal for heat which arises in the injection composition 11 during the injection molding. A tube system 12 can be included as a supplement, with it being possible to circulate coolant in the directions of arrows 13, 14 in accordance with FIG. 2.

Figure 4:
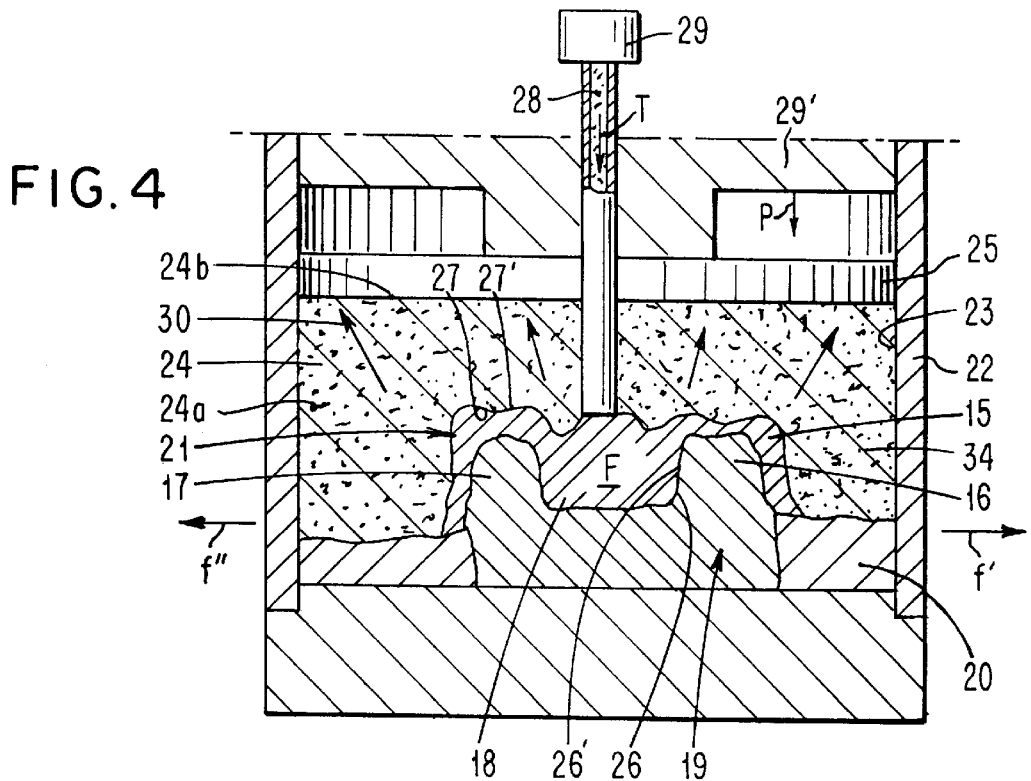
FIG. 4 shows a second embodiment of the tool in vertical section.

FIG. 4 shows an example of a complicated shape which can be injection molded, consisting, for example, of a dental bridge shell 15 which has to be applied to a base which is arranged in the human body and is formed from tooth remnants (implants, etc.), which tooth remnants are represented by 16 and 17 in FIG. 4. In the present case, the dental bridge has to be attached to two tooth remnants 16 and 17 and extend over the space 18 for a tooth which has been removed. The tooth remnants are symbolized or reproduced by a first model 19 which constitutes a copy of the tooth remnants (or equivalent). The shapes of the tooth remnants have been transferred to the first model using a copying process which can be of a known type. The first model is anchored in a known manner to a first tool part 20. A second model 21 is applied to the first model. The shape of the second model is produced in a known manner.

A member 22, which can have a cylindrical shape, is applied to the tool part 20. The inner space of the member forms a space 23 for a wet composition 24, which is applied to the space 23 in viscous form. The wet composition can be subjected to mechanical pressure using a compressing member 25 (disc). The wet composition contains 50 percent by weight of a metallic or alloy powder for providing the heat-removal function. The wet composition is solidified in the space by means of a chemical reaction. During this reaction, the solvent (water) in the wet composition is driven off and forms pores (a porous wall) in tool part 34. After the wet composition has solidified in the space, the tool parts 20 and 34 are separated and the model 21 is removed. With the removal of the model 21, a molding space F is formed in which a first delimitation surface is constituted by the upper surface 26' of the base 19 and a second delimitation surface 27 is constituted by the upper surface 27' of the second model. The tool part is returned to the position shown in FIG. 4 and the injection molding composition 28 is pressed or injected into the molding space F using an injection member 29, which can be of a known type.

The injection pressure T can be between 1–200 bar. Compression of the wet composition 24 is effected using a tool part 29'. The tool parts 20 and 34, and the member 22, are arranged to absorb lateral displacement forces f', f" which can arise due to the injection molding composition 28 being injected, thereby guaranteeing precision in the injection-molded product. Heat removal takes place, as described above, by means of the heat-removing particles 24a which are included in the solidified wet composition. Air (gas) which is trapped in the molding space is conducted away via the porosity in the tool part 34 in the directions of the arrows 30. The disc 25 does not seal the end surface 24b of the upper tool part 34 tightly, and air can be conducted away upwards, as is also the case for the removal of solvent from the wet composition.

Example I of an Injection Molding Composition Containing $H_2O_3$ Powder

A ceramic powder, aluminum oxide, Alcoa SG 16, VSA, was treated in accordance with the following procedure: 150 g of powder were weighed in and, in a first step, it was heat-treated at 150° C. for 3 hours in air in order to remove chemisorbed water; after that, the powder was left to cool in a desiccator. The loss of mass after this treatment was found to be 0.53%. In a second step, the powder was hydrophobicized in an HD-polyethylene container, with 3 g (1.96% by weight) of finely powdered stearic acid (KEBO) being added, on a drum bench for 3 hours using 1 kg of aluminum oxide milling media. A melt was prepared from 30.0 g of paraffin wax (KEBO, melting point: 62–64° C.) and 2.0 g of stearic acid, of identical quality as that described above, at a temperature of 120° C. An injection-moldable composition which was obtained by mixing this melt and the hydrophobicized ceramic powder had a dry matter content of 81.2% by weight, which corresponds to 50.1% by volume of aluminum oxide. A corresponding test was carried out using an identical Alcoa SG 16 ceramic powder which was neither heat-treated nor hydrophobicized. In this case, all the stearic acid was added to the paraffin wax melt so that the paraffin wax/stearic acid ratio corresponded to that in the above case, i.e. approximately 6:1. An injection-moldable composition which was obtained by mixing this melt and the untreated ceramic powder had a dry matter content of 78.0% by weight, which corresponds to 45.2% by volume of aluminum oxide.

Example II of an Injection Molding Composition Containing $Al_2O_3$ Powder

An injection molding composition was prepared having an $Al_2O_3$/MgO powder content of 48% by volume: a mixture of 405 grams of $Al_2O_3$ powder (Al6SG, ALCOA, USA) and 2 grams of MgO as sintering aid (MERCK, GERMANY) was heat-treated in a heating chamber at 300° C. for one hour, after which the powder was hydrophobicized with 10 grams of stearic acid by being treated in an HD-polyethylene container together with $Si_3N_4$ spheres on a drum bench. The stearic [lacuna] at a temperature of 70° C. The composition was homogenized at 70° C. for two hours by means of propeller stirring.

The composition was poured into the filling trough, which had been preheated to 70° C., of a medium-pressure injection molder (MPIM) (GO CERAM HB, Sweden). Components were injection-molded using molding tools as described in the examples below. The components were then placed on a powder bed of coarse-grained $Al_2O_3$ for controlled elimination of the organic additives in an RCE is (Rate-Controlled Extraction) Binding Agent Remover (GO CERAM HB, Sweden) in air. The components were then sintered (baked) to dense bodies at 1650° C. for one hour, and in an atmosphere of air, in a super kanthal kiln.

Example III of an Injection Molding Composition Containing Stainless 316 Steel Powder An injection molding composition was prepared having a steel powder content of 68% by volume: 1877 grams of gas-atomized, unfractionated 316 steel powder (22 z,900 m, OSPREY, ENGLAND) were heat-treated in a heating chamber at 200° C. for one hour, after which the powder was hydrophobicized with 15 grams of stearic acid. The stearic acid-coated steel powder was stirred into a melt of 80 grams of paraffin and 5 grams of polyethylene, containing 17% by weight of ethylenebutyl acrylate, at a temperature of 75° C. The composition was homogenized at 75° C. for two hours by means of propeller stirring. Sedimentation experiments showed that the steel powder did not sediment, or sedimented much more slowly, and had a considerably lower tendency to separate out from the paraffin than in experiments without the addition of polyethylene.

The composition was poured into the filling trough, which had been preheated to 75° C., of a medium pressure injection molder (MPIM) (GO CERAM HB, Sweden). Components were injection-molded using molding tools which were made as described below. The components were then placed in a powder bed of coarse-grained $Al_2O_3$ for controlled elimination of the organic additives in an RCE (Rate-Controlled Extraction) Binding Agent Remover (GO CERAM HB, Sweden) in hydrogen. The components were then sintered (burnt) to dense bodies at 1350° C. for two hours, in vacuo, in a graphite resistance kiln.

Examples of Injection Molding Tools (comparison with state of the art)

Three injection-molding tools were manufactured in different materials, with all the tools being of the same design as depicted above. One tool was produced, by milling, entirely from black steel. For the other two tools, a plate was cast in acrylate plastic, with a metal cylinder being applied to the middle of the plate. The cylinder part, projecting up from the plastic, was covered with wax, thereby constituting the mold cavity. A slurry containing 70% by volume of hard plaster and 30% by volume of fine-grained aluminum powder was poured over the plastic plate together with the wax-covered metal cylinder. After solidification, the plaster was shaped and an inlet hole for the injection molding composition was bored in it. In the same way, a molding tool half was produced from a slurry containing 70% by volume of cement and 30% by volume of aluminum powder. The steel tool turned out to be ten times more expensive and took three times as long to manufacture as compared with the other two tools.

The tool part which is produced from a wet composition can also be prepared from ceramic/metallic powder mixtures containing a temporary binding agent. The required properties are obtained by driving off the temporary binding agent after the embedment and then baking the tool part at a high temperature. This temperature is chosen so that the metal melts and forms a network for efficient heat removal. At the same time, the co-sintered ceramic structure retains its shape and porous structure. The metal and the ceramic can preferably be selected so that the ceramic is bound at contact points (by means of so-called neck formation) at the same time as the metal begins to melt and thus form a heat-conducting network through the pore channel structure. Thus, what is characteristic is the production of a tool part from a wet composition without shrinkage and comprising metallic and ceramic mixtures.

The invention is not limited to the embodiment which has been shown above as an example, and can be subjected to modifications within the scope of the subsequent patent claims and the inventive concept.

What is claimed is:

1. A process for injection molding a dental product, the process comprising:
    utilizing a tool including a molding space for the dental product, a first model for a base of the dental product and a second model for a shell of the dental product;
    applying the first model to a first tool part for forming a first delimitation surface with an upper surface of the first model;
    applying the second model to the first model;
    arranging a member that forms a molding space around at least the first model;
    injecting a wet composition containing heat-conducting particles into the molding space such that the second model is enclosed by the wet composition;
    solidifying the wet composition, pores being established in the solidified wet composition;
    allocating a function of a second tool part to the solidified material, wherein the second tool part can cooperate with the first tool part and wherein a second delimitation surface of the molding space is formed by an upper surface of the second model;
    separating the first tool part and the second tool part;
    removing the second model;
    bring together the first tool part and the second tool part;
    introducing into the molding space a material for forming the dental product; and
    hardening the material for forming the dental product, wherein heat removal from the material for forming the dental product is effected by the heat-conducting particles, wherein gas trapped in the material for forming the dental product is conducted away by the pores established in the solidified wet composition, and wherein breaking of the product is prevented by well balancing the porosity of the solidified wet composition and a flexibility of the material for forming the dental product after solidification of the material.

2. The method according to claim 1, wherein the product is ceramic and/or metallic.

3. The method according to claim 1, wherein the material for forming the product is introduced into the molding space by injection or squeezing.

4. A device including an injection molding tool for use once or a few times for producing a sinterable ceramic and/or metallic product, said device comprising:
    at least one first tool part;
    at least one second tool part combinable with said at least one first tool part to form a molding space for said product, said at least one second tool part being made of a readily worked and form-stable material, containing pores and admixed heat-conducting particles and being produced using a wet composition;
    a wet composition-enclosing member that can engage the at least one first tool part during production of the at least one second tool part; and
    a unit that can be connected to the at least one second tool part and can be arranged with the at least one first tool part for absorbing internal lateral displacement forces arising during squeezing or injection of an injection molding composition;
    wherein said injection molding tool is adapted to receive an injection molding composition containing a ceramic and/or metallic powder that is introduced into the injection molding tool with low or medium pressure for forming the product; and
    wherein said pores and said admixed heat-conducting particles conduct away heat generated during molding and gas trapped in the molding space, said pores also provide a well-balanced porosity for effecting conduction of the gas and, together with a flexibility in the injection molding composition as solidified, permit the product to be separated from the at least one first tool part and the at least one second tool part without braking.

5. The device according to claim 4, wherein the injection molding composition as solidified has a modulus of elasticity of greater than 1 GPa.

6. The device according to claim 4, wherein the heat-conducting particles comprise aluminum or aluminum alloy particles.

7. The device according to claim 6, wherein the heat-conducting particles comprise 30% to 80% by volume of the wet composition.

8. The device according to claim 6, wherein the heat-conducting particles comprise 20% to 40% by volume of the wet composition.

9. The device according to claim 4, wherein the heat-conducting particles comprise 30% to 80% by volume of the wet composition.

10. The device according to claim 4, wherein the heat-conducting particles comprise about 20% to about 40% by volume of the wet composition.

11. The device according to claim 4, wherein the heat-conducting particles establish an effective heat-removal network in the injection molding composition as solidified.

12. The device according to claim 4, wherein a porosity of the injection molding composition as solidified is 5% to 50% by volume.

13. The device according to claim 4, wherein a porosity of the injection molding composition as solidified is about 30% by volume.

14. The device according to claim 4, wherein a porosity of the injection molding composition as solidified effectively removes air existing in connection with molding of the product.

15. The device according to claim 4, wherein the readily worked and form-stable material comprises plaster, cement, or presintered ceramic powder.

16. The device according to claim 4, wherein the device produces a dental product.

17. The device according to claim 16, wherein the dental product is a dental bridge shell or dental prosthesis.

18. The device according to claim 4, wherein the wet composition is liquid or viscous at room temperature and wherein crystal formation or chemical reaction in the wet injection molding composition begins during mixing of the wet composition.

19. An injection molding tool for producing a product, the tool comprising:

a first tool part;

a second tool part mutually combinable and separable from the first tool part, the first tool part and the second tool part defining a molding space for a shell for receiving an injection molding composition when combined, the second tool part being formed from a solidified wet composition including pores and heat-conducting particles, the pores conducting away gas from the molding composition and help to prevent breaking the molding composition upon solidification and separation from the second tool part, and the heat-conducting particles removing heat during introduction of the molding composition into the molding tool;

a first model of a base supported by the first tool part such that an upper surface of the first model forms a first delimitation surface for the molding space;

a second model corresponding to a shape of the shell for application to the first model, the second tool part being formed by applying the wet composition at least around and enclosing the second model when the second model is positioned on the first model, wherein the second model is removable from the first model to form the molding space.

20. The tool according to claim 19, wherein the product is a shell for a ceramic and/or metallic product and/or ceramic and/or metallic prosthesis that can be anchored to a base.

* * * * *